United States Patent
Haragsim et al.

(12)

(10) Patent No.: US 6,277,371 B1
(45) Date of Patent: Aug. 21, 2001

(54) **BIOLOGICAL CONTROL OF VARROA MITES IN HONEYBEE HIVES WITH *HIRSUTELLA THOMPSONII***

(76) Inventors: Oldrich Haragsim, Chudenicka 1065/7, 10200 Prague 10 (CZ); Vaclav Ruzicka, 2910 Glenmore Road North, Kelowna, British Columbia (CA), V1V 2B6

( * ) Notice: Subject to any disclaimer, the term of this patent is extended or adjusted under 35 U.S.C. 154(b) by 0 days.

(21) Appl. No.: 09/574,933

(22) Filed: May 19, 2000

Related U.S. Application Data

(60) Provisional application No. 60/135,158, filed on May 20, 1999.

(51) Int. Cl.[7] .......................... A01N 65/00; A01N 25/00; C12N 1/14
(52) U.S. Cl. ....................... 424/93.5; 424/405; 435/254.1
(58) Field of Search ................................. 424/93.5, 195.1, 424/405; 435/254.1

(56) References Cited

U.S. PATENT DOCUMENTS 4,752,468 * 6/1988 Kennedy et al. ....................... 424/93

5,227,162 * 7/1993 Ferrari ................................ 424/195.1

OTHER PUBLICATIONS

Leszczynski et al., *Ochr. Rosl.* (29, No. 5, 5–9,), 1985.*

"*Hirsutella thompsonii*, a fungal pathogen of mites. II. Host–pathogen interactions", By U. Gerson, R. Kenneth and T. I. Muttath, *Ann. appl. Biol.* (1079), 91, 29–40.

"Microbial control of the Citrus Rust Mite with the Mycoacaricide, Mycar®", C. W. McCoy and T. L. Couch., Reprinted from the *Florida Entomologist*, vol. 65, No. 1, Mar. 1982.

"Tazonomy of the Acarine Parasite *Nirsutella Thompsonii*", Robert A. Samson and Kerry L. O'Donell., Reprinted from *Mycologia*, vol. LXXII, No. 2, pp. 359–377, Mar.–Apr., 1980.

* cited by examiner

*Primary Examiner*—David M. Naff
*Assistant Examiner*—Mike Meller
(74) *Attorney, Agent, or Firm*—Reidlaw, L.L.C.; John S. Reid

(57) ABSTRACT

The present invention includes the method of treating an infestation of Varroa mites in a honeybee colony including the steps of: (a) mixing a culture of *Hirsutella Thompsonii* fungus with a spreadable carrier media so as to form a carrier suspension; and, (b) dispersing the carrier suspension into the brood comb of a honeybee hive.

10 Claims, 2 Drawing Sheets

BIOLOGICAL CONTROL OF VARROA MITES IN HONEYBEE HIVES WITH *HIRSUTELLA THOMPSONII*

CROSS REFERENCE TO RELATED APPLICATION

This application claims priority from United States Provisional Patent Application No. 60/135,158 filed May 20, 1999 titled Biological Control of Varroa Mites.

FIELD OF THE INVENTION

This invention relates to the treatment of honeybees against parasitic mites by the use of a fungus and in the form of dust, wetable powder, liquid, or any other means of transfer of the active ingredient into the brood nest of beehives.

BACKGROUND OF THE INVENTION

It is known that honeybees, Apis Mellifera, may be plagued by parasitic mites and in particular by Varroa mites, Varroa Jacobsoni. The parasite feeds from the bees blood after attaching itself firmly to the body. A large shield-like hard casing protects the Varroa's vulnerable underside. Once attached, the parasite is virtually untouchable within the bee hive environment. Once inside the hive, other bees are quickly affected. Blood loss leads to lethargy, and with a decline in worker bees collecting pollen, the honey output declines. The hive itself can be completely wiped out in some cases within a few months. Conventionally, control of such parasitic mites in bee hives has been by mechanical evaporative distribution of formic acid, or by the use of pesticides such as Apistan™ (active ingredient Fluvalinate) or Taktivar™ (active ingredient Armitraz). The formic acid method of control of parasitic mites is typically laborious, requiring repeated maintenance and replenishment. The pesticide method of control of parasitic mites results in the mites building up a resistance to such pesticides, reducing their effectiveness.

Consequently, it is an object of the present invention to provide for the treatment of honeybees against Varroa mites by the use of a biological control namely the use of the acarine parasite *Hirsutella thompsonii*.

Commercially, *Hirsutella thompsonii* may be found as the active ingredient of a mycoacaricide, at one time produced under the trade-marks Mycar™ and, earlier, ABG6065, by Abbott Laboratories of North Chicago, Ill., U.S.A. As reported by McCoy and Couch in their publication entitled "Microbial Control of the Citrus Rust Mite with the Mycoacaricide, Mycar®" (the Florida Entomologist, Volume 65, Number 1, March 1982), Mycar™ as a wetable powder or dust was effective in stimulating premature fungal epizootics in citrus rust mite, *Phyllocoptruta oleivora*, populations in Valencia orange groves in central and south Florida. *Hirsutella thompsonii*, the active ingredient of Mycar™, was established on treated fruit and foliage via the particulate residue which supplied a substrate for mycelial growth and subsequent conidiogensis by the fungus. McCoy reported excellent crop protection was achieved with Mycar™ and a Mycar-oil combination in field trials.

McCoy and O'Donnell in their publication "Taxonomy of the Acarine Parasite *Hirsutella thompsonii*" (Mycologia, Volume LXXII, No. 2, pages 359–377, March–April, 1980) report that *Hirsutella thompsonii* is an important fungal pathogen of the citrus rust mite and other eriophyoid mites and that *Hirsutella thompsonii* appears to be a specific pathogen of various species of Acari which inhabit a wide range of plants throughout the world. These are plant mites, not mites on living organisms. The prior art does not report finding these mites on living organisms.

Gerson et al report ("*Hirsutella thompsonii*, a fungal pathogen of mites" Appl Biol (1979), 91, 29–40) that plant feeding mites are susceptible to *Hirsutella thompsonii* but that other mite orders were not infected by Hirsutella Thompsonii suggesting specificity of this fungus for one mite order—the Prostigmata.

What is neither taught nor suggested in the prior art and which is the subject of the present invention, is that *Hirsutella thompsonii* in the form of dust, wetable powder, liquid, or other carrying transfer media, may be used against mites on living organisms, specifically mites on honeybees, for example, by being applied into the honeybee's brood nest or food supply, and when so applied acts as a pathogen against a living organism, in particular, the Varroa mite which feeds on other living organisms, i.e. honeybees, rather than against other mites which feeds on plants and fruit.

SUMMARY OF THE INVENTION

In summary, in the present invention the method of treating an infestation of Varroa mites in a honeybee colony includes the steps of:

(a) mixing a culture of Hirsutella Thompsonii fungus with a spreadable carrier media so as to form a carrier suspension; and, (b) dispersing the carrier suspension into a honeybee brood.

The carrier media may be a fluid such as water wherein, in one method of the present invention, *Hirsutella thompsonii* is mixed with the water into a concentration of approximately 5 million spores of *Hirsutella thompsonii* per milliliter of water.

The carrier media may also be a dust or a wetable powder. The fungus is grown on a growing media such as soya flour or wheat bran or the like. The resulting culture and growing media are dried and ground into a dust or wetable powder containing a concentration of the fungus approximately or exceeding $8 \times 10^5$ spores per gram of the carrier suspension.

The step of dispersing the carrier suspension delivers the spores to each honeybee hive being treated.

DETAILED DESCRIPTION OF PREFERRED EMBODIMENT

Figure 1:
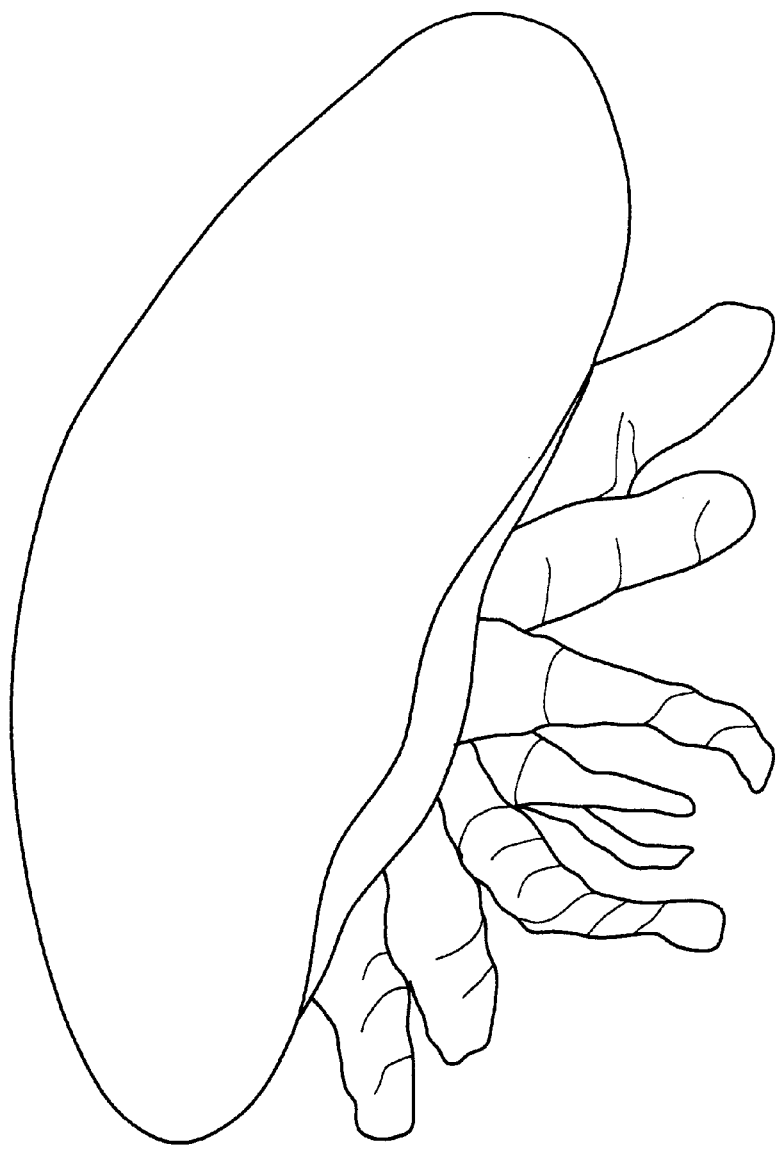
FIG. 1 is, in enlarged perspective view, a Varroa mite.

FIG. 1 is an illustration of a Varroa mite. An adult Varroa mite is typically 1–1½ mm in diameter.

In one method of the present invention, small amounts of Mycar™ dust, a powder which contains *Hirsutella thompsonii* as an active ingredient, were blown into an uncapped brood comb, 2–3 grams per beehive. The Mycar™ was a culture of *Hirsutella thompsonii* spores grown on a soya flour based growing media. Once dried and ground the Mycar™ had a concentration of approximately $8 \times 10^5$ spores per gram. Blowing the Mycar™ in the brood resulted in no young mites being subsequently found alive in the cells, although in early trials the adult mites on the honeybees were still present. It was determined that Mycar™ prevents the reproductive stage of the Varroa mite from occurring within the capped brood cells. In trials, the honeybees in all stages did not show a negative effect from the application of the Mycar™.

Samples of inactive Mycar™ powder were tested to prove that active material *Hirsutella thompsonii* fungus is responsible for control of the reproduction cycle of Varroa mites.

Figure 2:
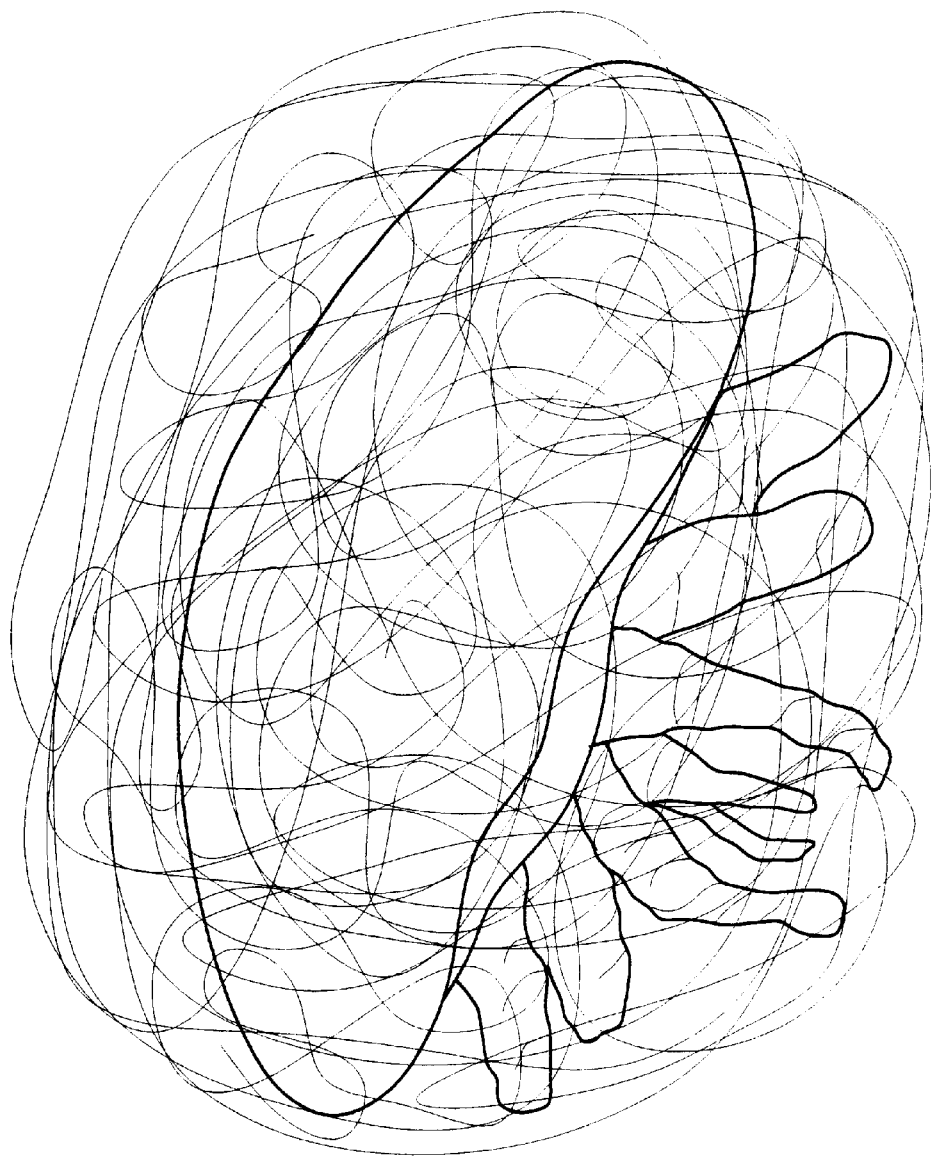
FIG. 2 is, in enlarged perspective view, the Varroa mite of FIG. 1, covered in a growth of *Hirsutella thompsonii* fungus mycelia.

A culture of active Hirsutella Thompsonii may also be grown on wheat bran or the like. In testing, the fungus was grown and a sterilized Varroa mite was let to walk on the surface of the fungus to be infected by fungus spores. FIG. 2 is an illustration of a Varroa mite covered in the fungus mycelia. The mite subjected to the test died within 72 hours and showed growth of mycelia from the underside of the mite's body in 12 days providing proof that *Hirsutella thompsonii* will kill the Varroa mite.

In an alternative method of the present invention, spores of *Hirsutella thompsonii* were washed off the growing plates into a distilled water so as to form a suspension containing approximately 5 million spores per milliliter. Each subsequently treated hive resulted in 85 to 100% of the hive infested cells not having reproduction of mites. Only dead offspring and dead adult mites were found on treated hives.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of treating an infestation of Varroa mites in a honeybee colony comprising the steps of:

(a) mixing a culture of *Hirsutella Thompsonii* fungus with a spreadable carrier media so as to form a carrier suspension; and, (b) dispersing said carrier suspension into the brood comb of a honeybee hive.

2. The method of claim 1 wherein said carrier media is a fluid.

3. The method of claim 2 wherein said fluid is water.

4. The method of claim 3 wherein said *Hirsutella thompsonii* is mixed with said water into a concentration of approximately 5 million spores of said *Hirsutella Thompsonii* per milliliter of said water.

5. The method of claim 1 wherein said carrier media is a dust.

6. The method of claim 1 wherein said carrier media is a wetable powder.

7. The method of claim 5 wherein said step of dispersing said carrier suspension approximately delivers a concentration of at least $8 \times 10^5$ spores per gram of carrier suspension to each honeybee hive being treated.

8. The method of claim 6 wherein said step of dispersing said carrier suspension approximately delivers a concentration of at least $8 \times 10^5$ spores per gram of carrier suspension to each honeybee hive being treated.

9. The method of claim 7 wherein 2–3 grams of said carrier suspension are delivered to each bee hive.

10. The method of claim 8 wherein 2–3 grams of said carrier suspension are delivered to each bee hive.

* * * * *